United States Patent

Berkowitz

[11] Patent Number: 6,051,721
[45] Date of Patent: Apr. 18, 2000

[54] RING E-MODIFIED ANALOGUES OF(-)-PODOPHYLLOTOXIN AND ETOPOSIDE AND A METHOD FOR THEIR SYNTHESIS

[75] Inventor: David Berkowitz, Lincoln, Nebr.

[73] Assignee: The Board of Regents of the University of Nebraska, Lincoln, Nebr.

[21] Appl. No.: 08/942,640

[22] Filed: Oct. 2, 1997

[51] Int. Cl.[7] .................. C07D 307/77; C07D 307/80
[52] U.S. Cl. ........................................... 549/298
[58] Field of Search ............................. 549/298

[56] References Cited

U.S. PATENT DOCUMENTS

| | | | |
|---|---|---|---|
| 4,122,092 | 10/1978 | Kende et al. | 260/340.5 R |
| 4,567,253 | 1/1986 | Durst et al. | 536/18.1 |
| 4,644,072 | 2/1987 | Vyas et al. | 549/433 |
| 4,788,216 | 11/1988 | Leander et al. | 514/468 |
| 4,965,348 | 10/1990 | Saulnier et al. | 536/17.2 |
| 5,011,948 | 4/1991 | Vyas et al. | 549/298 |
| 5,132,322 | 7/1992 | Lee et al. | 514/468 |
| 5,300,500 | 4/1994 | Lee et al. | 514/232.5 |
| 5,332,811 | 7/1994 | Lee et al. | 544/148 |
| 5,338,867 | 8/1994 | Choy et al. | 549/298 |
| 5,541,223 | 7/1996 | Lee et al. | 514/468 |

FOREIGN PATENT DOCUMENTS

| | | |
|---|---|---|
| 0 297 594 | 1/1989 | European Pat. Off. . |
| 0 304 086 | 2/1989 | European Pat. Off. . |
| 0 305 972 | 3/1989 | European Pat. Off. . |

OTHER PUBLICATIONS

M.G. Saulnier, et al., "E-ring Desoxy Analogues of Etopside" *J. Med. Chem.*, vol. 32, (7), pp. 1418–1420, 1989.

A. Haber, "Synthesis of a Podophyllotoxin Analog Using a Novel Iodotrimethylsilane Mediated Fragmentation", *Tetrahedron Lett.*, vol. 30, (41), pp. 5537–5538, 1989.

A.G. González, et al., "Synthesis of New Aryltetralin Lignans", *Tetrahedron*, vol. 42, (14), pp. 3899–3904, 1986.

C. T–L. Lee, et al., "Anti–AIDS Agents.29.[1] Anti–HIV Activity of Modified Podophyllotoxin Derivatives", *Bioorganic & Medicinal Chemistry Letters*, vol. 7, (22), pp. 2897–2902, 1997.

Berkowitz et al., "Enantioselective Entry into Benzoxabicyclo[2.2.1]heptyl Systems via Enzymatic Desymmetrization: Toward Chiral Building Blocks for Lignan Synthesis," *Tetrahedron: Assymetry*, vol. 7, No. 6, pp. 1577–1580, 1996.

Berkowitz et al., "Chemoenzymatic and Ring E–Modular Approach to the (–)–Podophyllotoxin Skeleton. Synthesis of 3',4',5'–Tridemethoxy–(–)podophyllotoxin," *J. Am. Chem. Soc.*, vol. 118, No. 39, pp. 9426–9427, 1996.

*Primary Examiner*—Ba K. Trinh
*Attorney, Agent, or Firm*—Banner & Witcoff, Ltd.

[57] ABSTRACT

A process of preparing ring E-modified analogues of (–)-podophyllotoxin as potential new chemotherapeutic agents. The process generates corresponding analogues of (–)-podophyllotoxin, itself, and allows new molecular interactions in the southern hemisphere (ring E) of the molecule. A method of preparing enantiomerically enriched compounds of the formula (I) and (II):

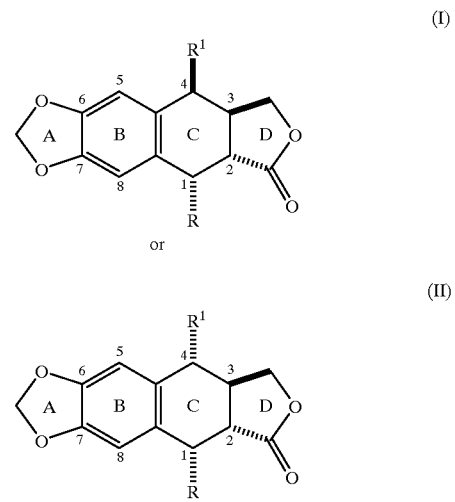

wherein R is:

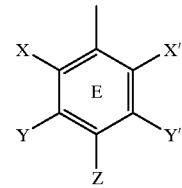

wherein X, X', Y, Y' and Z are ring E substituents and $R^1$ is one of a)–e) below.

a) —OH,
b) an ether or glycoside,
c) a substituted or unsubstituted amine or aniline,
d) a $C_2$–$C_8$ alkenyl group, preferably —$CH_2CH=CH_2$,
e) a $C_1$–$C_8$ alcohol, preferably —$CH_2CH_2CH_2OH$.

The process produces enantiomerically enriched compounds which do not occur naturally and are not readily available from (–)-podophyllotoxin.

27 Claims, No Drawings

RING E-MODIFIED ANALOGUES OF (-)-PODOPHYLLOTOXIN AND ETOPOSIDE AND A METHOD FOR THEIR SYNTHESIS

BACKGROUND OF THE INVENTION

Podophyllotoxin is a naturally occurring podophyllum lignan isolated from the roots of the apple mandrake tree. In 1946, podophyllotoxin was found to function as an antimitotic by inhibiting microtubule formation. Shortly thereafter, this lignan was examined as a potential antitumor agent, but was found to exhibit prohibitive toxicity in Phase I cancer trials. More recently, podophyllotoxin has been proposed as a medicinal agent for the treatment of psoriasis, malaria and rheumatoid arthritis (U.S. Pat. No. 4,788,216 (1988).

In the 1960's, medicinal chemists at Sandoz developed several promising semisynthetic derivatives of podophyllotoxin. Two of these, etoposide (VP-16), and teniposide (VM-26), showed promise as antitumor agents and so were developed further. Clinical trials began in 1967 for teniposide, and in 1971 for etoposide. The latter drug has been extensively employed as a chemotherapeutic ever since. Etoposide appears to act by promoting topoisomerase II-mediated DNA strand scission. The appearance of etoposide resistance, both through alterations in topo II and through MDR, underscores the importance of developing fundamentally new types of analogues. Its side effects appear to limited to myelosuppression, which may be controlled by carefully regulating dosage.

Etoposide has displayed remarkable efficacy as a single agent in the treatment of small cell lung cancer, testicular cancer, several leukemias and Kaposi's sarcoma (the tumor most closely associated with AIDS). More recently, etoposide has been identified as a very good candidate for the treatment of life-threatening cytomegalovirus (CMV) infections. The spectrum of carcinomas for which etoposide is effective has been expanded notably in recent years through the practice of combination therapy. Thus, encouraging clinical reports have appeared relating the application of etoposide to the treatment of cancers of the cervix, ovary, breast and prostate, as well as advanced Hodgkin's disease.

The clinical success of etoposide has also resulted in efforts to develop etoposide analogues, particularly in recent years. However, probably due to the lag in enantioselective total synthetic efforts in the area, etoposide analogues bearing modified aglycon moieties have been lacking. Instead, most efforts have focused upon semisynthesis, especially variation of the carbohydrate sector (thioetoposide and NK-61 1) or prodrug synthesis (e.g. etopophos (BMY-40481)). K. -H. Lee has been particularly prolific in this regard, having published a long series of papers describing largely "northern hemisphere" modifications of the natural product. This continues to be an active research area.

The chemistry leading from (-)-podophyllotoxin to etoposide has been well worked out. However, the path from (±)-podophyllotoxin to etoposide requires a tedious resolution step and is therefore not practical. Even so, most chemical syntheses of podophyllotoxin to date have led to racemic product.

SUMMARY OF THE INVENTION

With the synthetic route to the (-)-podophyllotoxin skeleton that constitutes the process of the present invention, previously unavailable ring E-modified analogues of etoposide can be constructed as potential new chemotherapeutic agents of this structural family. In addition, the process generates corresponding analogues of (-)-podophyllotoxin, itself. The process of the present invention allows new molecular interactions in the southern hemisphere (ring E) of the molecule.

The process of the present invention is directed to a method of preparing enantiomerically enriched compounds of the formulas (I) and (II):

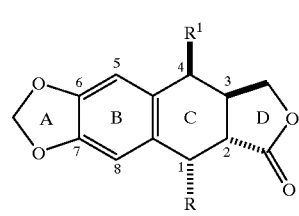

or

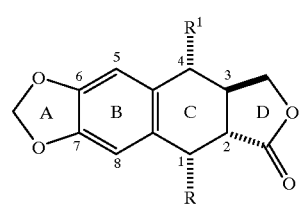

wherein R is:

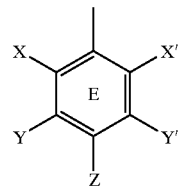

wherein X, X', Y, Y' and Z are ring E substituents and $R^1$ is one of a)–e) below.

a) —OH,
b) an ether or glycoside,
c) a substituted or unsubstituted amine or aniline,
d) a $C_2$–$C_8$ alkenyl group, preferably —$CH_2CH=CH_2$,
e) a $C_1$–$C_8$ alcohol, preferably —$CH_2CH_2CH_2OH$.

The present invention is also directed to enantiomerically enriched compounds which do not occur naturally and are not readily available from (-)-podophyllotoxin.

DETAILED DESCRIPTION OF THE PREFERRED EMBODIMENTS

Prior to the present invention, all asymmetric approaches to the (-)-podophyllotoxin framework employed a chiral auxiliary. It was discovered that enantiomerically enriched 3',4',5'-tridemethoxy-(-)-podophyllotoxin could be synthesized, which is the ring-E fully deoxygenated analogue of (-)-podophyllotoxin. The process of the present invention differs from previous methods by installing the ring E late in the sequence, so as to permit convenient variation of this important sector of the molecule. Absolute stereochemistry is introduced catalytically, by means of an enzyme-mediated desymmetrization of an advanced meso intermediate.

The key steps in this process are: (i) elaboration of an enzymatically-derived, enantiomerically enriched, monoester into, a key Michael acceptor, (ii) systematic synthetic variation of ring E structure in the (−)-podophyllotoxin framework through conjugate addition to that Michael acceptor (iii) aglycon glycosylation (or appendage of other O-, N- and C-centered $R^1$ groups) to produce etoposide analogues.

In accordance with the present invention, enantiomerically enriched compounds corresponding to the formula (I) or (II) below are prepared. Enantiomerically enriched means that the enantiomeric ratio is at least 95:5, preferably at least 97:3, prior to recrystallization.

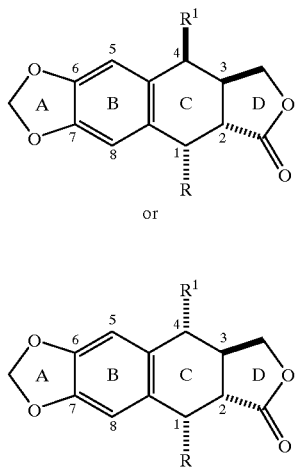

wherein R is:

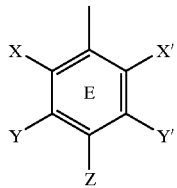

X, X', Y, Y' and Z may each be X, X', Y, Y' and Z may be hydrogen; deuterium; tritium; a $C_1-C_8$ saturated or unsaturated, alkyl or cycloalkyl group; a hydroxyl group; an ether-protected hydroxyl group bearing a $C_1-C_8$ saturated or unsaturated alkyl or cyclic alkyl group; a carboxylate ester-protected hydroxyl group derived from a $C_1-C_8$ saturated or unsaturated, cyclic or acyclic, carboxylic acid; a hydroxyl group protected as a phosphate mono-, di- or triester, the di-, or triester having $C_1-C_4$ saturated or unsaturated alkyl group(s); a phosphonate mono- or diester-protected hydroxyl group derived from a $C_1-C_8$ saturated or unsaturated, cyclic or acyclic, phosphonic acid wherein the diester also contains a $C_1-C_4$ saturated or unsaturated alkyl group; a phosphinate ester-protected hydroxyl group derived from a phosphinic acid bearing two $C_1-C_8$ saturated or unsaturated, cyclic or acyclic, alkyl groups; a hydroxyl group protected as a sulfate mono- or diester bearing a $C_1-C_4$ saturated or unsaturated alkyl group; a hydroxyl group protected as a sulfonate ester derived from a sulfonic acid bearing a $C_1-C_8$ saturated or unsaturated, cyclic or acyclic, alkyl group; an ammo group; a primary or secondary amine bearing 1 to 2 $C_1-C_4$ saturated or unsaturated alkyl group(s), respectively; a carboxamide-protected, unsubstituted or primary amino group bearing a $C_1-C_4$ saturated or unsaturated alkyl group and derived from a $C_1-C_8$ saturated or unsaturated, cyclic or acyclic, carboxylic acid; a carboxylic acid; a carboxylate ester bearing a $C_1-C_4$ saturated or unsaturated alkyl group; a phosphonic acid; a phosphonate mono- or diester bearing 1 to 2 $C_1-C_4$ saturated or unsaturated alkyl group(s), respectively; a phosphinic acid having a $C_1-C_8$ saturated or unsaturated, cyclic or acyclic, alkyl group or ester bearing a $C_1-C_4$ saturated or unsaturated alkyl group; a formyl group; an acetyl group; a benzoyl group; a carboxamide group derived from ammonia, or a primary or secondary amine bearing 1 to 2 $C_1-C_4$ saturated or unsaturated alkyl group(s), respectively; a sulfhydryl group; a thioether bearing a $C_1-C_8$ saturated or unsaturated, cyclic or acyclic, alkyl group; a sulfonic acid, a sulfonate ester bearing a $C_1-C_4$ saturated or unsaturated alkyl group; an alkylsulfonyl group bearing a $C_1-C_8$ saturated or unsaturated, cyclic or acyclic, alkyl group; a phenylsulfonyl group; a sulfoxide bearing a $C_1-C_8$ saturated or unsaturated, cyclic or acyclic, alkyl group; a phenylsulfoxide; a phenylseleno group; a phenylselenoxide; an azide; a halogen; a cyano group; a nitro group; a nitroso group; a diazonium group; or a trifluoromethyl group.

An unexpected result of the present invention is that many types of substitutents are available for ring E. This is obtained by the late addition of ring E during synthesis of the compounds.

$R^1$ is one of a) —OH b) an ether, such as —OCH$_2$CH=CH$_2$, —OCH$_2$Ph, and —OCH$_2$CH$_2$NH$_2$, or glycoside, preferably

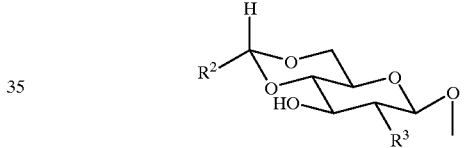

wherein $R^2$ is methyl or 2-thienyl, and $R^3$ is —OH or N(CH$_3$)$_2$;

c) a substituted or unsubstituted amine or aniline including, but not limited to:

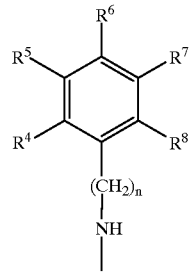

where n=0–4, and $R^4$, $R^5$, $R^6$, $R^7$, and $R^8$ are each independently selected from the group consisting of hydrogen; a saturated or unsaturated $C_1-C_8$ alkyl or cycloalkyl, optionally substituted with a halogen or hydroxy; a halogen, or a hydroxy; a $C_1-C_8$ alkoxy; a $C_1-C_8$ alcohol; an ether having $C_1-C_8$ alkyl groups; a carboxylate ester having $C_1-C_8$ alkyl groups; an amide; a carboxylic acid; an amine, optionally substituted with one or more $C_1-C_4$ alkyl group(s); NH$_2$.HCl, NH$_2$.HAc, NH$_2$.½H$_2$SO$_4$, NH$_2$.⅓H$_3$PO$_4$, SO$_2$H, SO$_2$NH$_2$; a cyano group; a phosphate acid or ester having $C_1$–$C_8$ alkyl groups; a phosphonic acid or ester having $C_1$–$C_8$ alkyl groups; a nitro group; a nitroso group; an azide; a sulfone; a sulfoxide; a diazonium salt, phenyl, a substituted phenyl, phenoxy, substituted phenoxy, anilinyl, substituted anilinyl, cyclohexyl, piperidine, or a heterocyclic ring; or any two of $R^4$–$R^8$ may together form a heterocyclic ring.

d) a $C_2$–$C_8$ alkenyl group, preferably —$CH_2CH$=$CH_2$;

e) a $C_1$–$C_8$ alcohol, preferably —$CH_2CH_2CH_2OH$.

Examples of suitable $R^1$ substituents include the substituents disclosed in U.S. Pat. Nos. 5,132,322; 5,300,500; 5,332,811; 5,541,223, which are each incorporated herein by reference, and which are included within the present invention.

In addition, the hydrogens at carbons 5 and 8 can be replaced with a halogen, such as Br, as disclosed by U.S. Pat. No. 5,132,322, which is incorporated by reference.

The method begins with a compound of formula (a) which can be obtained, for example, by the process described in *Tetrahedron: Asymmetry* 1996, 7(6), 1577–1580 (June 1996 issue) beginning from piperonal. The key meso diacetate is readily constructed in seven steps therefrom in which an isobenzofuran Diels-Alder reaction is the key step. PPL (porcine pancreatic lipase in crude form from Sigma Chemical Co.) selectively deacetylates the (R)-acetoxymethyl arm of the diacetate to form the compound of formula (a). Meso diacetate (compound (a)) is a substrate for a number of acyl transferases. PPL gives especially good results, in terms of both chemical and optical yield, furnishing (+)(a) (95% ee) in 66% yield (83% yield corrected for recovered diacetate).

The compound of formula (a)

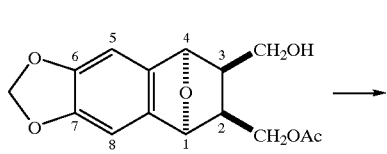

(a)

is converted by silylation, deacetylation, and oxidation to produce a compound of formula (b) without loss of optical activity. Silylation occurs with a silylating agent, $R^9X$, including but not limited to TIPSCl (triisopropylsilyl chloride), TBDMSCl (tert-butyldimethylsilyl chloride), and TBDPSCl (tert-butyldiphenylsilyl chloride), in the presence of an appropriate base such as imidazole or $NEt_3$. Deacetylation is carried out under standard conditions (e.g. $K_2CO_3$, MeOH or Na, MeOH or $NH_3$, MeOH). The aldehyde is then oxidized to the corresponding aldehyde under mild two-electron oxidation conditions (e.g. Swern or Moffatt oxidation (DMSO as oxidant), Ley oxidation (TPAP= tetrapropylammonium perrhuthenate as oxidant) or Dess-Martin oxidation (Dess-Martin periodinane as oxidant.))

The compound of formula (b)

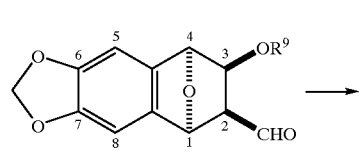

(b)

wherein $R^9$ is a silyl protecting group, is converted to a compound of formula (c) by retro-Michael ring opening and protection of the $C_4$—OH followed by aldehyde oxidation. The ring opening occurs under typical Michael addition conditions (such as NaOMe and MeOH). The protection step must be carried out under basic conditions (to avoid aromatization) in the presence of an alkyl halide (e.g. allyl bromide, benzyl bromide) or halomethyl ether (e.g. BOMBr, SEMCl). Aldehyde oxidation proceeds smoothly under Lindgren conditions ($NaClO_2$ as oxidant) to give (c). The efficient retro-Michael ring-opening of (b) unveils the (methylenedioxy)cinnamyl system as the vehicle for late installation of ring E, the key step in this process.

The compound of formula (c)

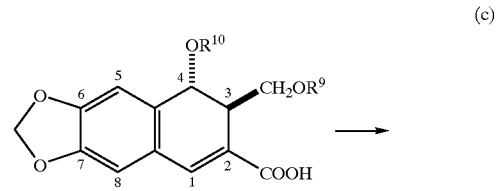

(c)

wherein $R^{10}$ is a $C_4$ protecting group, such as SEM (2-trimethylsilyl)ethoxymethyl), BOM (benzyloxymethyl), benzyl, or allyl, is converted to a compound of formula (d) by transformation of the carboxylic acid into an acyl oxazolidinone functionality. This requires carboxyl activation (e.g. with carbonyl diimidazole) and then condensation with a metalated oxazolidinone to give (d).

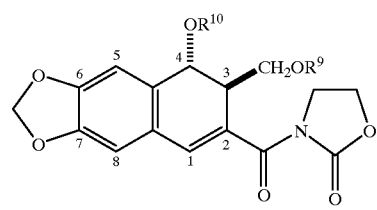

(d)

As for relative stereochemistry, Michael acceptor (d) is designed to promote re face conjugate addition. In fact, $Cu^I$-mediated conjugate addition of RMgBr to (d) occurs exclusively from the desired re face and is quite efficient. Thus, the compound of formula (d) is converted to a compound of formula (e) by $Cu^I$-mediated conjugate addition of RMgBr at a temperature of −10 to 0° C. Because this introduction of ring E occurs late in this synthesis, the procedure provides for the convenient synthesis of a variety of ring E-congeners of (−)-podophyllotoxin.

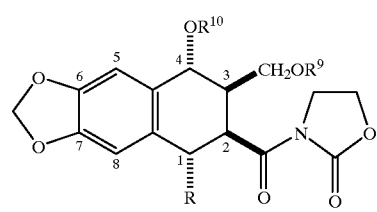

(e)

The compound of formula (e) is converted to a compound of formula (f) by chemoselective silyl ether deprotection by heating with a fluoride source, such as TBAF, and cyclization to produce the corresponding lactone.;

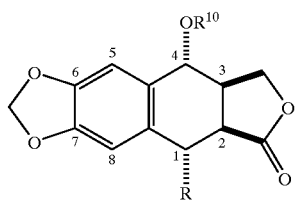

(f)

The compound of formula (f) is converted to a compound of formula (I) by generation and kinetic quenching of a $C_2$-enolate and deprotection of the $C_4$—OH. If $R^{10}$=SEM, then it is particularly advantageous to use modified Kim conditions during this step. S. Kim et al. "Uses Butanethiol, $MgBr_2$ in $Et_2O$ to Deprotect SEM Ethers" Synlett (1991) 183–184. Modified conditions substituted ethanethiol (EtSH) for butanethiol.

In any of the above steps, an appropriate solvent is used as is well within the skill of the art.

The present invention is also directed to an enantiomerically enriched compound corresponding to the formula (I) or (II):

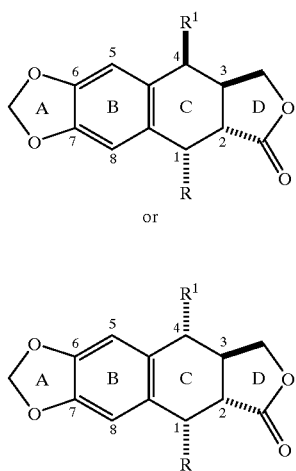

(I)

or (II)

wherein R is:

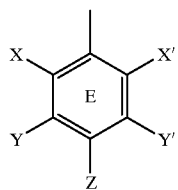

X, X', Y, Y' and Z may each be hydrogen; deuterium; tritium; a $C_1$–$C_8$ saturated or unsaturated, alkyl or cycloalkyl group; a hydroxyl group; an ether-protected hydroxyl group bearing a $C_1$–$C_8$ saturated or unsaturated alkyl or cyclic alkyl group; a carboxylate ester-protected hydroxyl group derived from a $C_1$–$C_8$ saturated or unsaturated, cyclic or acyclic, carboxylic acid; a hydroxyl group protected as a phosphate mono-, di- or triester, the di-, or triester having $C_1$–$C_4$ saturated or unsaturated alkyl group(s); a phosphonate mono- or diester-protected hydroxyl group derived from a $C_1$–$C_8$ saturated or unsaturated, cyclic or acyclic, phosphonic acid wherein the diester also contains a $C_1$–$C_4$ saturated or unsaturated alkyl group; a phosphinate ester-protected hydroxyl group derived from a phosphinic acid bearing two $C_1$–$C_8$ saturated or unsaturated, cyclic or acyclic, alkyl groups; a hydroxyl group protected as a sulfate mono- or diester bearing a $C_1$–$C_4$ saturated or unsaturated alkyl group; a hydroxyl group protected as a sulfonate ester derived from a sulfonic acid bearing a $C_1$–$C_8$ saturated or unsaturated, cyclic or acyclic, alkyl group; an amino group; a primary or secondary amine bearing 1 to 2 $C_1$–$C_4$ saturated or unsaturated alkyl group(s), respectively; a carboxamide-protected, unsubstituted or primary amino group bearing a $C_1$–$C_4$ saturated or unsaturated alkyl group and derived from a $C_1$–$C_8$ saturated or unsaturated, cyclic or acyclic, carboxylic acid; a carboxylic acid; a carboxylate ester bearing a $C_1$–$C_4$ saturated or unsaturated alkyl group; a phosphonic acid; a phosphonate mono- or diester bearing 1 to 2 $C_1$–$C_4$ saturated or unsaturated alkyl group(s), respectively; a phosphinic acid having a $C_1$–$C_8$ saturated or unsaturated, cyclic or acyclic, alkyl group or ester bearing a $C_1$–$C_4$ saturated or unsaturated alkyl group; a formyl group; an acetyl group; a benzoyl group; a carboxamide group derived from ammonia, or a primary or secondary amine bearing 1 to 2 $C_1$–$C_4$ saturated or unsaturated alkyl group(s), respectively; a sulfhydryl group; a thioether bearing a $C_1$–$C_8$ saturated or unsaturated, cyclic or acyclic, alkyl group; a sulfonic acid, a sulfonate ester bearing a $C_1$–$C_4$ saturated or unsaturated alkyl group; an alkylsulfonyl group bearing a $C_1$–$C_8$ saturated or unsaturated, cyclic or acyclic, alkyl group; a phenylsulfonyl group; a sulfoxide bearing a $C_1$–$C_8$ saturated or unsaturated, cyclic or acyclic, alkyl group; a phenylsulfoxide; a phenylseleno group; a phenylselenoxide; an azide; a halogen; a cyano group; a nitro group; a nitroso group; a diazonium group; or a trifluoromethyl group;

with the proviso that only one of Y, Y', and Z can be a hydroxyl or an ether- or ester-protected hydroxyl group; and R is one of a) —OH;

b) ether or glycoside, preferably

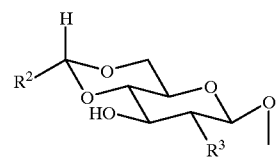

wherein $R^2$ is methyl or 2-thienyl, and $R^3$ is —OH or $N(CH_3)_2$;

c) a substituted amine or aniline, as defined above;

d) a $C_2$–$C_8$ alkenyl group, preferably —$CH_2CH$=$CH_2$;

e) a $C_1$–$C_8$ alcohol, preferably —$CH_2CH_2CH_2OH$.

The present invention is also directed to an enantiomerically enriched compound corresponding to the formula (I) or (II):

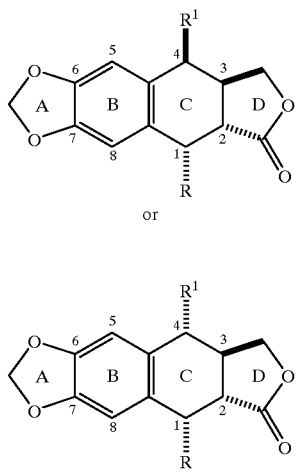

wherein R is:

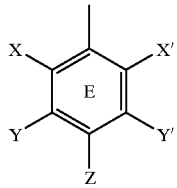

X, X', Y, Y' and Z may each be hydrogen; deuterium; tritium; a $C_1$–$C_8$ saturated or unsaturated, alkyl or cycloalkyl group; a hydroxyl group; an ether-protected hydroxyl group bearing a $C_1$–$C_8$ saturated or unsaturated alkyl or cyclic alkyl group; a carboxylate ester-protected hydroxyl group derived from a $C_1$–$C_8$ saturated or unsaturated, cyclic or acyclic, carboxylic acid; a hydroxyl group protected as a phosphate mono-, di- or triester, the di-, or triester having $C_1$–$C_4$ saturated or unsaturated alkyl group(s); a phosphonate mono- or diester-protected hydroxyl group derived from a $C_1$–$C_8$ saturated or unsaturated, cyclic or acyclic, phosphonic acid wherein the diester also contains a $C_1$–$C_4$ saturated or unsaturated alkyl group; a phosphinate ester-protected hydroxyl group derived from a phosphinic acid bearing two $C_1$–$C_8$ saturated or unsaturated, cyclic or acyclic, alkyl groups; a hydroxyl group protected as a sulfate mono- or diester bearing a $C_1$–$C_4$ saturated or unsaturated alkyl group; a hydroxyl group protected as a sulfonate ester derived from a sulfonic acid bearing a $C_1$–$C_8$ saturated or unsaturated, cyclic or acyclic, alkyl group; an amino group; a primary or secondary amine bearing 1 to 2 $C_1$–$C_4$ saturated or unsaturated all group(s), respectively; a carboxamide-protected, unsubstituted or primary amino group bearing a $C_1$–$C_4$ saturated or unsaturated alkyl group and derived from a $C_1$–$C_8$ saturated or unsaturated, cyclic or acyclic, carboxylic acid; a carboxylic acid; a carboxylate ester bearing a $C_1$–$C_4$ saturated or unsaturated alkyl group; a phosphonic acid; a phosphonate mono- or diester bearing 1 to 2 $C_1$–$C_4$ saturated or unsaturated alkyl group(s), respectively; a phosphinic acid having a $C_1$–$C_8$ saturated or unsaturated, cyclic or acyclic, alkyl group or ester bearing a $C_1$–$C_4$ saturated or unsaturated alkyl group; a formyl group; an acetyl group; a benzoyl group; a carboxamide group derived from ammonia, or a primary or secondary amine bearing 1 to 2 $C_1$–$C_4$ saturated or unsaturated alkyl group(s), respectively; a sulfhydryl group; a thioether bearing a $C_1$–$C_8$ saturated or unsaturated, cyclic or acyclic, alkyl group; a sulfonic acid, a sulfonate ester bearing a $C_1$–$C_4$ saturated or unsaturated alkyl group; an alkylsulfonyl group bearing a $C_1$–$C_8$ saturated or unsaturated, cyclic or acyclic, alkyl group; a phenylsulfonyl group; a sulfoxide bearing a $C_1$–$C_8$ saturated or unsaturated, cyclic or acyclic, alkyl group; a phenylsulfoxide; a phenylseleno group; a phenylselenoxide; an azide; a halogen; a cyano group; a nitro group; a nitroso group; a diazonium group; or a trifluoromethyl group;

with the proviso that only two Y, Y' and Z can be a hydroxyl or an ether-or ester-protected hydroxyl group; and R is one of a) —OH;

b) ether or glycoside, preferably

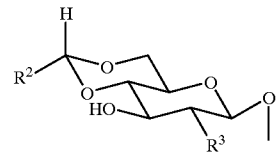

wherein $R^2$ is methyl or 2-thienyl, and $R^3$ is —OH or $N(CH_3)_2$;

c) a substituted or unsubstituted amine or aniline as defined above;

d) a $C_2$–$C_8$ alkenyl group, preferably —$CH_2CH$=$CH_2$;

e) a $C_1$–$C_8$ alcohol, preferably —$CH_2CH_2CH_2OH$;

except the following compounds:

X and X'=H, Y=—$OCH_3$, Y'=H, —$NH_2$, —$N^+$≡N, Cl, Br, I, Z=—OH;

X and X'=H, Y=$OCH_3$, Y'=$OCH_3$, Z=H, Cl or Br; and

X and X'=H, Y=OH, Y'=H, Z=$OCH_3$.

The above exception excludes known derivatives of (−)-podophyllotoxin and congeners in which either the 4'- or the 3'-methoxy groups are deoxygenated, as the literature (Saulmier, M. G. et al. 1989) teaches that these transformations are readily performed, albeit in several steps. Also excluded are the 3'-amino and 3'-diazonium derivatives (and obvious Sandmeyer coupling products therefrom) en route to the 3 '-deoxy compound. Finally, the 4'-chloro and 4'-bromo derivatives are excluded as these may be obtained by subjecting (−)-podophyllotoxin to $PCl_5$ (Ayers et al. J. C. S. Perkin I, 1972, pp 1350–1355). The 3'-deoxy, 4-demethyl derivative of (−)-podophyllotoxin is excluded as it occurs naturally in plants (Wichers, H. J. et al. Phytochem. Vol. 30, 1991, pp3601–3604) and is known as NC 370.

The compounds prepared in accordance with the above method are suitable for use in pharmaceutical compositions along with a pharmaceutically acceptable carrier.

EXAMPLES

The invention will be further described by reference to the following examples. These examples should not be construed in any way as limiting the invention to anything less than that which is disclosed or which could have been obvious to anyone skilled in the art.

Example 1

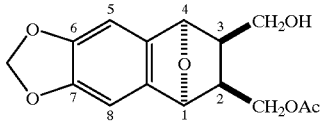

Compound (a) (14.5 g, 49.6 mmol) was dissolved in DMF (75 mL) and imidazole (7.4 g, 0.11 mol) was added. After stirring for 15 min, the reaction mixture was taken to ice bath. TIPSCl (11.7 mL, 54.6 mmol)/DMF (70 mL) was cannulated at 0° C., then the reaction mixture was stirred at room temperature under Ar for 9 h. The reaction mixture was diluted with $Et_2O$ (1 L) and washed with $NaHCO_3$ (3×150 mL) and HO (3×150 mL). The organic layer was dried over $MgSO_4$ and concentrated to give a silyl ether (b)(22.3 g, 100%).

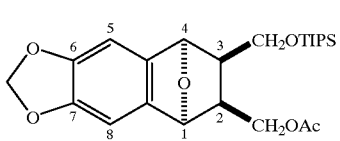

$^1$H NMR (360 MHz $CDCl_3$) δ1.03 (d, J=3 Hz, 18H), 1.03–1.22 (m, 3H), 2.06 (s, 3H), 2.76–2.77 (m, 3H), 3.14 (app t, J=10 Hz, 1H), 3.40–3.43 (m, 1H), 3.78 (dd, J=5, 11 Hz, 1H), 5.24(d, J=4 Hz, 1H), 5.33 (d, J=3 Hz, 1H), 5.94 (d, J=1 Hz, 1H), 5.97(d, J=1 Hz, 1H), 6.74 (s, 1H), 6.83 (s, 1H); $^{13}$C NMR (75 MHz, $CDCl_3$) δ 12.5, 18.6, 21.5, 40.2, 44.3, 61.8, 63.3, 82.3, 82.9, 101.8, 103.6, 104.1, 136.9, 137.5, 147.1, 147.2, 171.3; $[\alpha]^{21}_D$=+3.0° (c 0.9, $CHCl_3$). HRMS (FAB, 3-NOBA, LiI) calcd for $C_{24}H_{36}O_6SiLi$ 455.2442, obsd 455.2443.

To a solution of starting acetate (7.10 g, 15.8 mmol) in MeOH (60 mL) was added $K_2CO_3$ (438 mg, 3.17 mmol). The resulting suspension was stirred for 4 hours at room temperature. Then, $Et_2O$ (100 mL) and Dowex 50×8 resin ($H^+$-form; 1.8 g) were added and stirring was continued for 1 h. Filtration and concentration yielded the desired alcohol (c) (6.43 g, 100%) as an oil:

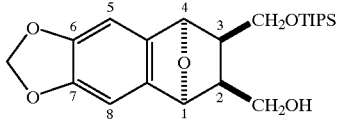

$^1$H NMR (300 MHz, $CDCl_3$) δ 0.98–1.07 (m, 21H), 2.79–2.85 (m, 2H), 2.97–3.11 (m, 2 H),3.17(dd, J=5,11 Hz, 1H),3.31(dd, J=6, 10 Hz, 1H),5.19(d, J=4 Hz, 1H),5.20 (d, J=5 Hz, 1H), 5.96 (s, 2H), 6.73 (s, 1H), 6.76 (s, 1H); $^{13}$C NMR (75 MHz, $CDCl_3$) δ 12.4, 18.6, 44.4, 44.5, 61.1, 62.1, 82.0, 82.1, 101.9, 103.3, 103.4, 137.3, 137.6, 147.0, 147.1; IR (ATR) 3419 cm$^{-1}$; $[\alpha]^{21}_D$=−26.8° (c 1.3, $CHCl_3$). HRMS (FAB, 3-NOBA, LiI) calcd for $C_{22}H_{34}O_5SiLi$ 413.2336, obsd 413.2341.

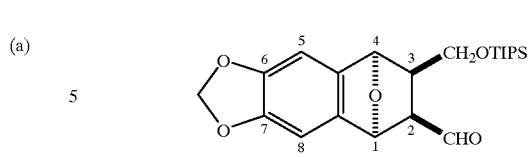

To a solution of oxalyl chloride (2.96 g 23.3 mmol) in $CHCl_2$ (11.6 mL) at −78° C. was added a solution of DMSO (2.06 g, 26.4 mmol) in $CH_2Cl_2$ (9 mL) via cannula. After stirring for 10 min at −78° C., a solution of starting alcohol (6.30 g, 15.5 mmol) in $CH_2Cl_2$ (9 mL) was added, dropwise via cannula. After an additional 30 min at −78° C., a solution of $NEt_3$ (4.72 g, 46.5 mmol) in $CH_2Cl_2$ (6.5 mL) was added in the same manner. After 1 h at −78° C., additional $CH_2Cl_2$ was added to facilitate stirring (continued for another 1 h). $Et_2O$ (100 mL) was then added at −78° C. and the reaction mixture was allowed to warm to rt. The crude reaction mixture was then poured into $Et_2O$ (300 mL) and extracted sequentially with $H_2O$ (3×150 mL), sat'd $NH_4Cl$ (aqueous, 2×150 mL) and sat'd NaCl (aqueous, 150 mL). After drying ($MgSO_4$), filtration and evaporation, aldehyde (d) (6.09 g, 97%) was obtained: $^1$H NMR (300 MHz, $CDCl_3$) δ 0.97–1.20 (m, 21H), 2.99–3.12 (m, 2H), 3.22 (ddd, J=3, 5, 8 Hz, 1H), 3.46–3.51 (m, 1H), 5.38 (s, 1H), 5.40 (s, 1H), 5.96 (d, J=1 Hz, 1H),5.98(d, J=1 Hz, 1H),6.84(s, 1H),6.85(s, 1H),9.07(d, J=3 Hz, 1H); $^{13}$C NMR(125 MHz, $CDCl_3$) δ 12.6, 18.6, 47.3, 54.2, 62.8, 81.0, 82.7, 102.0, 103.9, 104.0, 136.9, 137.5, 147.4, 147.5, 202.5; $[\alpha]^{21}_D$=−26.3° (c 0.8, $CHCl_3$). HRMS (FAB, 3-NOBA, NaI) calcd for $C_{22}H_{32}O_5SiNa$ 427.1917, obsd 427.1925.

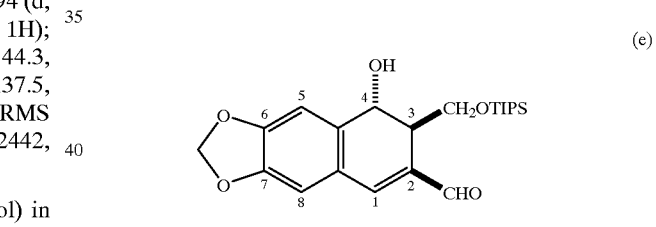

To a solution of aldehyde (e) (10.5 g, 26.0 mmol) in absolute MeOH (95 mL) at rt was added freshly prepared NaOMe in MeOH (300 mL of a 60 mM solution). After 24 h at rt, the reaction was monitored by TLC and additional NaOMe (3×20 mL) was added at ca. 2 h intervals, until no (e) remained. $H_2O$ (245 mL) was then added and $CO_2$ was bubbled through the solution until the pH reached 8 (pH paper). MeOH was removed in vacuo, and the resulting aqueous layer was extracted with $CH_2Cl_2$ (3×200 mL). The combined organics were dried ($MgSO_4$), filtered and evaporated to provide analytically pure product as a white solid (9.50 g, 90%): mp 87–89° C.; $^1$H NMR (500 MHz, $CDCl_3$) δ 0.93–1.03 (m, 21H), 1.74 (d, J=5 Hz, 1H), 3.17 (app t, J=10 Hz, 1H), 3.34 (ddd, J=2, 4, 6 Hz, 1H), 3.80 (dd, J=4, 10 Hz, 1H), 4.97 (app t, J=1 Hz, 1H), 6.01 (s, 1H), 6.02 (s, 1H), 6.83 (s, 1H), 6.93 (s, 1H), 7.24 (s, 1H), 9.61 (s, 1H); $^{13}$C NMR (125 MHz, $CDCl_3$) δ 12.5, 18.5, 43.4, 62.7, 70.0, 102.4, 109.8, 110.9., 125.3, 133.8, 136.0, 145.6, 148.8, 150.7, 192.9; IR (ATR) 3395, 1674, 1645 cm$^{-1}$; $[\alpha]^{21}_D$=+82.0° (c 1.0, $CHCl_3$); HRMS (FAB, 3-NOBA) calcd for $C_{22}H_{33}O_5Si$ [(M+H)$^+$] 405.2097, obsd 405.2096. Anal. Calcd for $C_{22}H_{32}O_5Si$: C, 65.31; H, 7.97. Found: C, 65.45; H, 7.98.

(f)

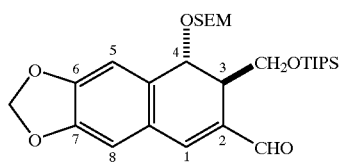

To a solution of starting alcohol (7.0 g, 17 mmol) in CH₂C₂ (140 mL) at 0° C. were added sequentially, diisopropylethylamine (9.0 mL, 52 mmol) and SEM chloride (4.6 mL, 26 mmol). The resulting reaction mixture was allowed to warm slowly to room temperature overnight and then poured into sat'd NaHCO₃ (aqueous, 150 mL). The aqueous layer was further extracted with CH₂Cl₂ (2×150 mL). After drying (MgSO₄), filtering and evaporating, the crude product was purified by SiO₂ chromatography (25 to 50% EtOAc-hexanes) to provide (f) (8.6 g, 93%): ¹H NMR (360 MHz, CDCl₃) δ 0.00 (s, 9H), 0.91–1.04 (m, 23H), 3.07 (app t, J=10 Hz, 1H), 3.41 (ddd, J=2, 4, 6 Hz, 1H), 3.46–3.62 (m, 2H), 3.70 (dd, J=5, 10 Hz, 1H), 4.58 (d, J=7 Hz, 1H), 4.65 (d, J=7 Hz, 1H), 4.98 (d, J=1 Hz, 1H), 6.01 (d, J=2 Hz, 1H), 6.02 (d, J=1 Hz, 1H), 6.84 (s, 1H), 6.90 (s, 1H), 7.23 (s, 1H), 9.60 (s, 1H); ¹³C NMR (75 MHz, CDCl₃) 6–0.8, 12.5, 18.6, 18.7, 41.1, 61.8, 65.7, 72.3, 92.4, 102.4, 109.9, 112.1, 126.3, 130.7, 136.5, 145.7, 148.7, 150.2, 192.9; IR (ATR) 1674 cm⁻¹; $[\alpha]^{21}_D$=+37.7° (c 0.9, CHCl₃). Anal. Calcd for C₂₈H₄₆O₆Si₂: C, 62.88; H, 8.67. Found: C, 63.00; H, 8.49.

(g)

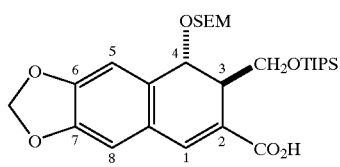

To a solution of aldehyde (f) (3.5 g, 6.5 mmol) in t-BuOH (130 mL) and 2-methyl-2-butene (35 mL) at room temperature was added a solution of NaClO₂ (5.4 g, 60 mmol) and NaH₂PO₄ (5.4 g) in H₂O (60 mL). After being allowed to stir at room temperature overnight, the reaction mixture was extracted with Et₂O (3×150 mL), dried and concentrated. Flash chromatography (0.5% MeOH-34.5% EtOAc-65% hexanes) provided the acid (g) (3.6 g, 100%). [On a larger scale, (f) (15.0 g, 28 mmol) gave the same acid in excellent yield (14.8 g, 95%)] ¹H NMR (360 MHz, CDCl₃) δ 0.00 (s, 9H), 0.92–1.12 (m, 23H), 3.13 (app t, J=10 Hz, 1H), 3.38 (ddd, J=1, 5, 6 Hz, 1H), 3.47–3.65(m, 2H),3.78(dd, J=4, 10 Hz, 1H),4.61 (d, J=7 Hz, 1H),4.67(d, J=7 Hz, 1H), 4.97 (d, J=2 Hz, 1H), 5.99 (d, J=1 Hz, 1H), 6.01 (d, J=1 Hz, 1H), 6.80 (s, 1H), 6.88 (s, 1H), 7.63 (s, 1H); ¹³C NMR (125 MHz, CDCl₃) 6–0.8, 12.6, 18.6, 18.7, 43.2, 62.0, 65.7, 72.6, 92.4, 102.2, 109.9, 112.0, 125.8, 126.5, 129.4, 139.1, 148.6, 149.6, 172.9; IR (ATR) 3854, 1676 cm⁻; $[\alpha]^{21}_D$=+78.3° (c 1.6, CHCl₃). HRMS (FAB, 3-NOBA, NaI) calcd for C₂₈H₄₆O₇Si₂Na 573.2680, obsd 573.2677.

(h)

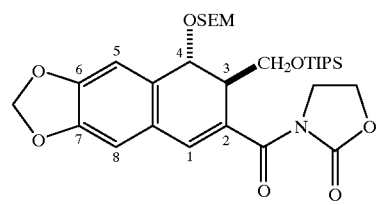

To a solution of starting acid (4.3 g, 7.8 mmol) in THF (20 mL) at room temperature was added carbonyl diimidazole (1.4 g, 8.6 mmol), whereupon gas evolution was immediately observed. After 3 h at room temperature, the reaction mixture was partitioned between Et₂O (50 mL) and H₂O (50 mL). The H₂O-layer was further extracted once with Et₂O (50 mL). The combined organics were dried and evaporated to provide the crude acyl imidazolide which was taken forward without further purification. The next transformation was generally carried out on a 100 mg–1 g scale, with the best yields being obtained on the smaller scales.

To a deoxygenated solution of 2-oxazolidinone (16 mg, 0.18 mmol) in THF (1 mL) at −78° C. was added n-BuLi (130 mL of a 1.4 M solution in hexanes, 0.18 mmol). The resulting reaction mixture was allowed to stir for 1 h at −78° C. Then a solution of acyl imidazolide (100 mg, 0.166 mmol) in THF (1 mL) was added, dropwise, via cannula at −78 ° C. After 4.5 h at −78° C., the reaction mixture was diluted with Et₂O (5 mL) and then extracted with KO (3×4 mL). The organic layer was dried (MgSO₄), filtered, concentrated and chromatographed (NEt₃-EtOAc-hexanes: 2:49:49) to yield (h) (62 mg, 60%). [On a larger scale, acyl imidazolide (1.8 g, 3.0 mmol) provided (h) (840 mg, 45%).] mp 110–112° C.; ¹H NMR (500 MHz, CDCl₃) 6−0.01 (s, 9H), 0.93–1.03 (m, 23H), 3.22 (app t, J=10 Hz, 1H), 3.44 (ddd, J=2, 6, 7 Hz, 1H), 3.52 (app dt, J=6, 10 Hz, 1H), 3.61 (app dt, J=6, 11 Hz, 1H), 3.71 (app dd, J=6, 10 Hz, 1H), 3.95 (ddd, J=6, 8, 10 Hz, 1H), 4.09–4.15 (m, 1H), 4.37–4.44 (m, 2H), 4.60 (d, J=7 Hz, 1H), 4.68 (d, J=7 Hz, 1H), 4.94 (d, J=2 Hz, 1H), 5.96 (d, J=2 Hz, 1H), 5.98 (d, J=1 Hz, 1H), 6.74 (s, 1H), 6.86 (s, 1H), 7.12 (s, 1H); ¹³C NMR (125 MHz, CDCl₃) δ −0.78, 12.5, 18.6, 18.7, 43.7, 44.7, 62.4, 62.8, 65.6, 71.7, 92.3, 102.2, 109.9, 112.0, 126.2, 127.1, 128.7, 138.0, 148.6, 149.4, 154.2, 170.2; IR (ATR) 1781, 1663 cm⁻¹; $[\alpha]^{21}_D$=+69.9° (c 3.0, CHCl₃). Anal. Calcd for C₃₁H₄₉NO₈Si₂: C, 60.06; H, 7.97; N, 2.26. Found: C, 60.19; H. 7.70; N, 2.32.

(i)

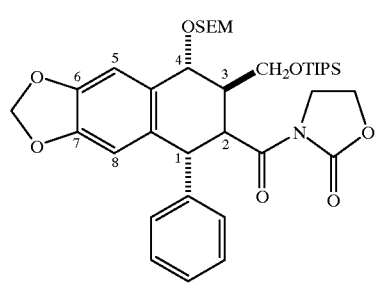

To a suspension of CuCN (1.62 g, 18.1 mmol) in THF (17 mL) and Me₂S (17 mL) at −78° C., was added PhMgBr (21.5 mL of a 1.0 M solution in Et₂O). The resulting mixture was allowed to stir 1.5 h at −78° C., whereupon a solution of (h) (1.40 g, 2.26 mmol) in THF (12.5 mL) was added via cannula. After 3 h at −40° C., sat'd NH₄Cl (aqueous, 40 mL)

was added, followed by Et$_2$O (75 mL). After further extraction of the aqueous layer with Et$_2$O (2×50 mL), the combined organics were dried (M$_g$SO$_4$), filtered and evaporated. Chromatography (25% EtOAc-hexanes) yielded (i) (1.23 g, 78%): $^1$H NMR (360 MHz, CDCl$_3$) δ 0.04 (s, 9H), 0.96–1.06 (m, 23H), 2.70–2.75 (m, 1H), 3.49 (dd, J=9, 10 Hz, 1H), 3.60–3.67 (m, 1H), 3.75 (dd, J=5, 11 Hz, 1H), 3.81–3.91 (m, 3 H), 4.19–4.31 (m, 2H), 4.44 (d, J=11 Hz, 1H), 4.80–4.86 (m, 2H), 4.87 (d, J=3 Hz, 1 H),4.93(d, J=7 Hz, 1H), 5.81(d, J=1 Hz, 1H),5.86(d, J=1 Hz, 1H),6.22(s, 1H), 6.73 (s, 1H), 7.21–7.23 (m, 5H); $^{13}$C NMR (125 MHz, CDCl$_3$) δ –0.7, 12.6, 18.6, 18.8, 42.4, 43.4, 44.0, 45.6, 61.5, 62.4, 65.7, 73.0, 93.1, 101.5, 110.0, 110.6, 127.1, 127.8, 129.0, 130.2, 133.6, 145.7, 146.7, 148.3, 153.2, 174.4; IR (ATR) 1784, 1695 cm$^{-1}$; [α]$^{21}_D$=–106.9° (c 3.6, CHCl$_3$). Anal. Calcd for C$_{37}$H$_{55}$NO$_8$Si$_2$: C, 63.67; H. 7.94; N, 2.01. Found: C, 63.72; H, 7.78; N, 1.86.

(j)

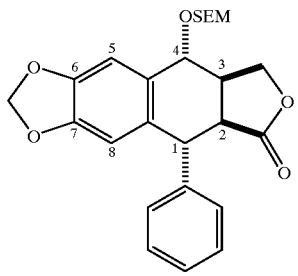

To a solution of (i) (647 mg, 928 mmol) in THF (5 mL) at room temperature was added TBAF (1.85 mL of a 1.0 M solution in THF). The resulting reaction mixture was heated at 40–50° C. for 5 h. After cooling to room temperature, the volatiles were evaporated in vacuo. The residue was taken up in dry PhH—CHCl$_3$ (1:1; 20 mL) and concentrated on a rotary evaporator to remove H$_2$O. This procedure was repeated twice. Then the crude product was partitioned between CH$_2$Cl$_2$ (40 mL) and sat'd NH$_4$Cl (aqueous, 40 mL). After further extraction of the aqueous layer with CH$_2$Cl$_2$ (2×40 mL), the crude product was subjected to SiO$_2$ chromatography (25% EtOAc-hexanes) to provide (i)(336 mg, 80%) as a white solid: mp 121–123° C.; $^1$H NMR (500 MHz, CDCl$_3$) δ 0.02 (s, 9H), 0.90–1.00 (m, 2H), 2.92–2.98 (m, 1H), 3.26 (dd, J=5, 10 Hz, 1H), 3.53–3.59 (m, 1H), 3.70–3.75 (m, 1H), 4.23 (d, J=5 Hz, 1H), 4.29 (dd, J=4, 10 Hz, 1H), 4.41 (dd, J=7, 9 Hz, 1H),4.50(d, J=7 Hz, 1H),4.71 (s, 1H),5.90(d, J=1 Hz, 1H),5.91(d, J=1 Hz, 1H), 6.39 (s, 1H), 6.88 (s, 1H), 6.39–7.33 (m, 5H); $^{13}$C NMR (125 MHz, CDCl$_3$) δ –0.8, 18.8, 41.5, 45.1, 45.7, 66.6, 70.6, 75.7, 94.7, 101.8, 107.8, 110.3, 127.5, 129.1, 129.2, 129.8, 132.1, 143.9, 147.4, 148.3, 178.7; IR (ATR) 1765, 1753 cm$^{-1}$; [α]$^{21}_D$=+106.5° (c 1.1, CHCl$_3$). Anal. Calcd for C$_{25}$H$_{30}$O$_6$Si: C, 66.05; H. 6.65. Found: C, 65.83; H, 6.49.

(k)

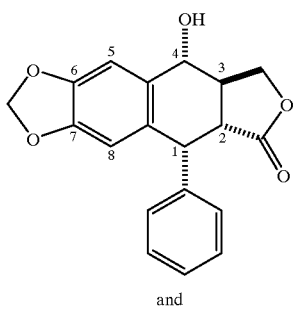

and (l)

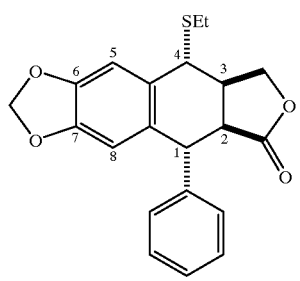

To a solution of diisopropyl amine (430 ML, 3.1 mmol) in THF (7 mL) at –78° C., was added n-BuLi (1.95 mL of a 1.4 M solution in hexanes, 2.7 mmol). After stirring for 30 min at 0° C., the resulting LDA solution was cooled to –78° C., whereupon a solution of (j) (700 mg, 1.54 mmol) in THF (8.5 mL) was added dropwise via cannula at –78° C. After stirring this solution for 90 min at –78° C., a suspension of freshly prepared pyridinium hydrochloride (890 mg, 7.7 mmol) in THF (3×2 mL) was added. The transfer was effected in three portions due to the limited solubility of the salt in THF. After allowing the reaction mixture to come to room temperature, it was poured into sat'd NH$_4$Cl (aqueous, 30 mL) and CHCl$_3$ (50 mL). Following a second extraction with CHCl$_3$ (50 mL), the organics were dried (MgSO$_4$), filtered, concentrated and flushed through an SiO$_2$ column (35% EtOAc-hexanes) to give a mixture of diastereomeric lactones (j) (656 mg, 94%; trans:cis=2:1 by $^1$H NMR). This diastereomeric mixture (650 mg, 1.43 mmol) was taken up in Et$_2$O ($_{11}$ mL) and PhH (2.7 mL). MgBr$_2$—Et$_2$O complex (554 mg 2.15 mmol) was added under Ar atmosphere in a glove bag. To the resulting solution at 0° C. was added EtSH (265 mL, 3.58 mmol) dropwise, via syringe. After 2 h at 0° C. and 6 h at room temperature, additional MgBr$_2$—Et$_2$O (170 mg, 0.66 mmol) and EtSH (100 mL; 1.35 mmol) were added, as before. After 3 h (0° C. to room temp), the reaction was quenched by the addition of sat'd NaHCO$_3$ (15 mL) and extracted thrice with CH$_2$Cl$_2$ (15 mL portions). The combined organics were dried (MgSO$_4$), filtered, and concentrated. Flash chromatography (25 to 50% EtOAc-hexanes) gave (k) (170 mg, 32%) in a first fraction, and (l) (220 mg, 47%) in a second fraction:

For (k): mp 180–182° C.; $^1$H NMR (500 MHz, CDCl$_3$) δ 1.95 (d, J=9 Hz, 1H), 2.71–2.80 (im, 1H), 2.86 (dd, J=5, 14 Hz, 1H), 4.08 (dd, J=9, 10 Hz, 1H), 4.57 (dd, J=7, 9 Hz, 1H), 4.63 (d, J=5 Hz, 1H), 4.77 (app t, J=9 Hz, 1H), 5.95 (s, 2H), 6.45 (s, 1H), 7.13–7.26 (m, 6H); $^{13}$C NMR (125 MHz, CD$_2$Cl$_2$/CD$_3$OD) δ 40.9, 44.6, 45.5, 72.4 (2C), 101.9, 106.9, 109.8, 127.4, 128.2, 131.3, 131.9, 134.6, 141.0, 148.0, 148.1, 176.0; IR (ATR) 3411, 1754 cm$^{-1}$; [α]$^{21}_D$=–154° (c 0.16, EtOH) Anal. Calcd for C$_{19}$H$_{16}$O$_5$: C, 70.36; H, 4.97. Found: C, 70.56; H, 5.16.

For l: $^1$H NMR (500 MHz, CDCl$_3$) δ 1.28 (app dt, J=1, 7 Hz, 3H), 2.58 (q, J=7, 15 Hz, 2H),2.86–2.88(m, 1H), 3.13 (dd, J=4, 8 Hz, 1H), 3.68 (d, J=8 Hz, 1H), 4.31 (d, J=4 Hz, 1H),4.36(dd, J=6, 10 Hz, 1H), 4.44(dd, J=2,9 Hz, 1H), 5.90(s, 1H), 5.91 (s, 1H), 6.35 (s, 1H), 7.17–7.34 (m, 6H); $^{13}$C NMR (75 MHz, CDCl$_3$) δ 15.1, 25.6, 40.5, 44.1, 46.3, 47.4, 72.4, 101.8, 108.9, 110.2, 127.6, 129.2, 129.4, 129.6, 131.4, 144.8, 147.6, 147.7, 177.7; IR (AIR) 1770 cm$^{-1}$; [α]$^{21}_D$=–55.4° (c 0.2, CHCl$_3$). HRMS (FAB, 3-NOBA, NaI) calcd for C$_{21}$H$_{20}$O$_4$SNa 391.0980, obsd 391.0977.

Example 2

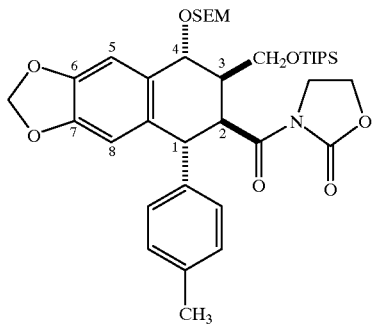

To a suspension of CuCN (0.58 g, 6.45 mmol) in THF (15 mL) and Me$_2$S (15 mL) at –10° C., was added p-CH$_3$C$_6$H$_5$MgBr (6.45 mL of a 1.0 M solution in Et$_2$O). The resulting mixture was allowed to stir 1 h at –10° C., whereupon a solution of h (example 1) (0.5 g, 0.81 mmol) in THF (15 mL) was added via cannula. After 20 min at –10° C., sat'd NH$_4$Cl (aqueous, 15 mL) was added, followed by Et$_2$O (25 mL). After further extraction of the aqueous layer with Et$_2$O (2×20 mL), the combined organics were dried (MgSO$_4$), filtered and evaporated. Chromatography (10% EtOAc-hexanes) yielded product (0.486 g, 84.7%).

Example 3

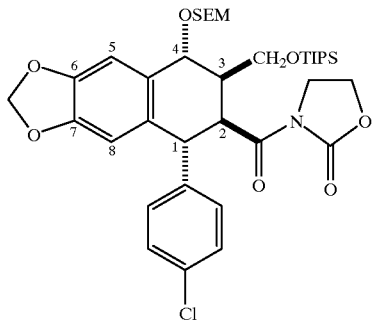

To a suspension of CuCN (0.87 g, 9.68 mmol) in THF (45 mL) at –10° C., was added p-ClC$_6$H$_5$MgBr (9.68 mL of a 1.0 M solution in THF). The resulting mixture was allowed to stir 1 h at –10° C., whereupon a solution of h (example 1) (0.75 g, 1.21 mmol) in THF (22.5 mL) was added via cannula. After 12 min at –10° C., sat'd NH$_4$Cl (aqueous, 20 mL) was added, followed by Et$_2$O (40 mL). After further extraction of the aqueous layer with Et$_2$O (2×25 mL), the combined organics were dried (MgSO$_4$), filtered and evaporated. Chromatography (10% EtOAc-hexanes) yielded product (0.66 g, 75%).

Example 4

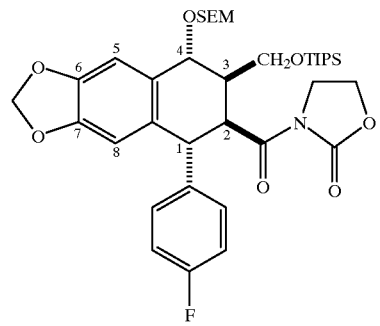

To a suspension of CuCN (0.87 g, 9.68 mmol) in THF (45 mL) at –10° C., was added p-FC$_6$H$_5$MgBr (9.68 mL of a 1.0 M solution in THF). The resulting mixture was allowed to stir 1 h at –10° C., whereupon a solution of h(example 1) (0.75 g, 1.21 mmol) in THF (22.5 mL) was added via cannula. After 2 h at –10° C., sat'd NH$_4$Cl (aqueous, 20 mL) was added, followed by Et$_2$O (40 mL). After further extraction of the aqueous layer with Et$_2$O (2×25 mL), the combined organics were dried (MgSO$_4$), filtered and evaporated. Chromatography (10% EtOAc-hexanes) yielded product (0.51 g, 59.0%).

Example 5

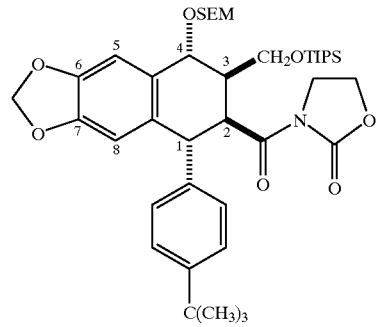

To a suspension of CuCN (1.445 g, 16.13 mmol) in THF (75 ML) at –10° C., was added p-tert-BuC$_6$H$_5$MgBr (8.07 mL of a 2.0 M solution in THF). The resulting mixture was allowed to stir 1 h at –10° C., whereupon a solution of h (example 1) (1.25 g, 2.02 mmol) in THF (37.5 mL) was added via cannula. After 20 min at –10° C., sat'd NH$_4$Cl (aqueous, 35 mL) was added, followed by Et$_2$O (70 mL). After further extraction of the aqueous layer with Et$_2$O (2×45 mL), the combined organics were dried (MgSO$_4$), filtered and evaporated. Chromatography (10% EtOAc-hexanes) yielded product (1.14 g, 75%).

It will be apparent to those skilled in the art that various modifications and variations can be made in the compositions and methods of the present invention without departing from the spirit or scope of the invention. Thus, it is intended that the present invention cover the modifications and variations of this invention provided they come within the scope of the appended claims and their equivalents.

What is claimed is:

1. A process for preparing an enantiomerically enriched compound corresponding to the formula (I) or (II):

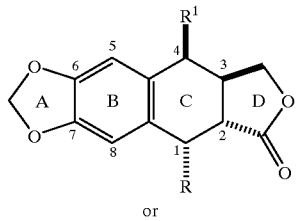
(I)

or

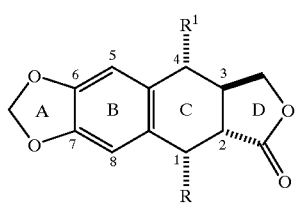
(II)

wherein R is:

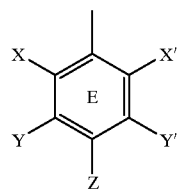

and X, X', Y, Y' and Z may each be hydrogen; deuterium; tritium; a $C_1$–$C_8$ saturated or unsaturated, alkyl or cycloalkyl group; a hydroxyl group; an ether-protected hydroxyl group bearing a $C_1$–$C_8$ saturated or unsaturated alkyl or cyclic alkyl group; a carboxylate ester-protected hydroxyl group derived from a $C_1$–$C_8$ saturated or unsaturated, cyclic or acyclic, carboxylic acid; a hydroxyl group protected as a phosphate mono-, di- or triester, the di-, or triester having $C_1$–$C_4$ saturated or unsaturated alkyl group(s); a phosphonate mono- or diester-protected hydroxyl group derived from a $C_1$–$C_8$ saturated or unsaturated, cyclic or acyclic, phosphonic acid wherein the diester also contains a $C_1$–$C_4$ saturated or unsaturated alkyl group; a phosphinate ester-protected hydroxyl group derived from a phosphinic acid bearing two $C_1$–$C_8$ saturated or unsaturated, cyclic or acyclic, alkyl groups; a hydroxyl group protected as a sulfate mono- or diester bearing a $C_1$–$C_4$ saturated or unsaturated alkyl group; a hydroxyl group protected as a sulfonate ester derived from a sulfonic acid bearing a $C_1$–$C_8$ saturated or unsaturated, cyclic or acyclic, alkyl group; an amino group; a primary or secondary amine bearing 1 to 2 $C_1$–$C_4$ saturated or unsaturated alkyl group(s), respectively; a carboxamide-protected, unsubstituted or primary amino group bearing a $C_1$–$C_4$ saturated or unsaturated alkyl group and derived from a $C_1$–$C_8$ saturated or unsaturated, cyclic or acyclic, carboxylic acid; a carboxylic acid; a carboxylate ester bearing a $C_1$–$C_4$ saturated or unsaturated alkyl group; a phosphonic acid; a phosphonate mono- or diester bearing 1 to 2 $C_1$–$C_4$ saturated or unsaturated alkyl group(s), respectively; a phosphinic acid having a $C_1$–$C_8$ saturated or unsaturated, cyclic or acyclic, alkyl group or ester bearing a $C_1$–$C_4$ saturated or unsaturated alkyl group; a formyl group; an acetyl group; a benzoyl group; a carboxamide group derived from ammonia, or a primary or secondary amine bearing 1 to 2 $C_1$–$C_4$ saturated or unsaturated alkyl group(s), respectively; a sulfhydryl group; a thioether bearing a $C_1$–$C_8$ saturated or unsaturated, cyclic or acyclic, alkyl group; a sulfonic acid, a sulfonate ester bearing a $C_1$–$C_4$ saturated or unsaturated alkyl group; an alkylsulfonyl group bearing a $C_1$–$C_8$ saturated or unsaturated, cyclic or acyclic, alkyl group; a phenylsulfonyl group; a sulfoxide bearing a $C_1$–$C_8$ saturated or unsaturated, cyclic or acyclic, alkyl group; a phenylsulfoxide; a phenylseleno group; a phenylselenoxide; an azide; a halogen; a cyano group; a nitro group; a nitroso group; a diazonium group; or a trifluoromethyl group; and $R^1$ is one of a) —OH;

b) an ether or glycoside;

c) a substituted or unsubstituted amine or aniline;

d) a $C_2$ to $C_8$ alkenyl group;

e) a $C_1$ to $C_8$ alcohol;

comprising subjecting a compound of formula (a);

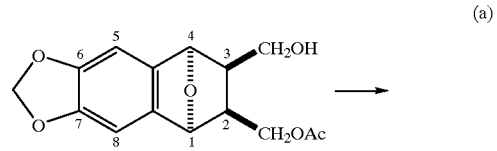
(a)

to silylation, deacetylation, and oxidation to produce a compound of formula (b)

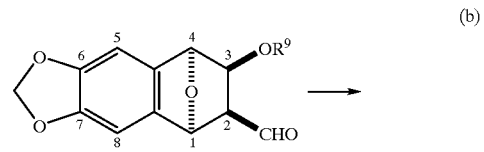
(b)

wherein $R^9$ is a silyl protecting group;

converting the compound of formula (b) to a compound of formula (c) by retro-Michael ring opening and protection of the $C_4$—OH followed by aldehyde oxidation

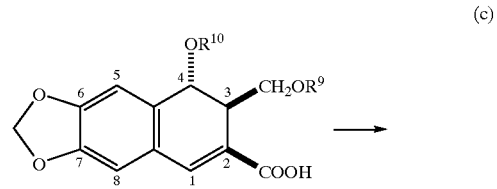
(c)

wherein $R^{10}$ is a $C_4$ protecting group;

converting the compound of formula (c) to a compound of formula (d) by transformation of the carboxylic acid into an acyl oxazolidinone functionality;

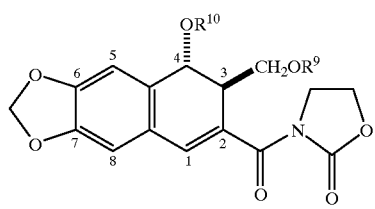

(d)

converting the compound of formula (d) to a compound of formula (e) by Cu$^I$-mediated conjugate addition of RMgBr at a temperature of −10 to 0° C.;

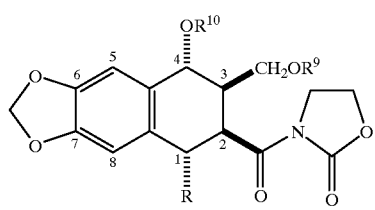

(e)

converting the compound of formula (e) to a compound of formula (f) by chemoselective silyl ether deprotection by heating with a fluoride source and cyclization to produce the corresponding lactone;

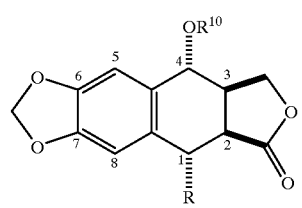

(f)

converting the compound of formula (f) to a compound of formula (I) by generation and kinetic quenching of a $C_2$ enolate and deprotection of the $C_4OH$.

2. The process according to claim 1 wherein $R^1$ is

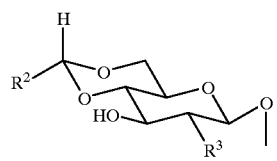

wherein R is methyl or thienyl, and $R^3$ is —OH or $N(CH_3)_2$.

3. The process according to claim 1 wherein $R^1$ is

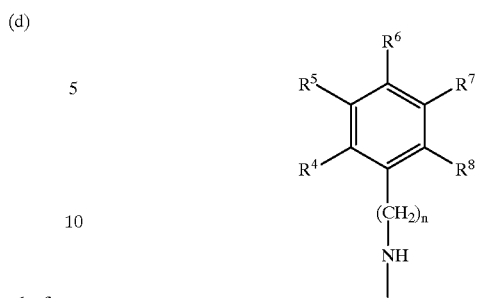

wherein n=0–4 and $R^4$, $R^5$, $R^6$, $R^7$, and $R^8$ are each independently selected from the group consisting of hydrogen; a saturated or unsaturated $C_1$–$C_8$ alkyl or cycloalkyl, optionally substituted with a halogen or hydroxy; a halogen, or a hydroxy; a $C_1$–$C_8$ alkoxy; a $C_1$–$C_8$ alcohol; an ether having $C_1$–$C_8$ alkyl groups; a carboxylate ester having $C_1$–$C_8$ alkyl groups; an amide; a carboxylic acid; an amine, optionally substituted with one or more $C_1$–$C_4$ allyl group(s); $NH_2.HCl$, $NH_2.HAc$, $NH_2.½H_2SO_4$, $NH_2.⅓H_3PO_4$, $SO_2K$ $SO_2NH_2$; a cyano group; a phosphate acid or ester having $C_1$–$C_8$ alkyl groups; a phosphonic acid or ester having $C_1$–$C_8$ alkyl groups; a nitro group; a nitroso group; an azide; a sulfone; a sulfoxide; a diazonium salt, phenyl, a substituted phenyl, phenoxy, substituted phenoxy, anilinyl, substituted anilinyl, cyclohexyl, piperidine, or a heterocyclic ring; or any two of $R^4$–$R^8$ may together form a heterocyclic ring.

4. The process according to claim 1 wherein the silylating agent is TIPSCl.

5. The process according to claim 1 wherein the oxidation is Swern oxidation.

6. The process according to claim 1 wherein $R^{10}$ is SEM.

7. The process according to claim 6 wherein the compound of formula (f) is converted to the compound of formula (I) under modified Kim conditions.

8. A process of converting a compound of formula (d)

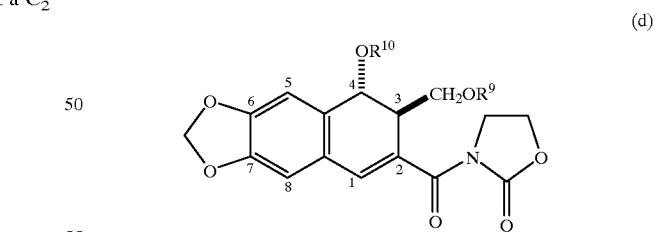

(d)

to a compound of formula (e) comprising Cu$^I$-mediated conjugate addition of RMgBr at a temperature of −10 to 0° C.

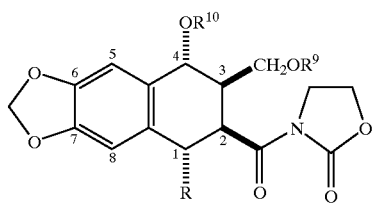

(e)

wherein R is

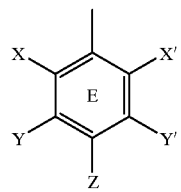

and X X', Y, Y' and Z may each be hydrogen; deuterium; tritium; a $C_1$–$C_8$ saturated or unsaturated, alkyl or cycloalkyl group; a hydroxyl group; an ether-protected hydroxyl group bearing a $C_1$–$C_8$ saturated or unsaturated alkyl or cyclic alkyl group; a carboxylate ester-protected hydroxyl group derived from a $C_1$–C, saturated or unsaturated, cyclic or acyclic, carboxylic acid; a hydroxyl group protected as a phosphate mono-, di- or triester, the di-, or triester having $C_1$–$C_4$ saturated or unsaturated alkyl group(s); a phosphonate mono- or diester-protected hydroxyl group derived from a $C_1$–C, saturated or unsaturated, cyclic or acyclic, phosphonic acid wherein the diester also contains a $C_1$–$C_4$ saturated or unsaturated alkyl group; a phosphinate ester-protected hydroxyl group derived from a phosphinic acid bearing two $C_1$–$C_8$ saturated or unsaturated, cyclic or acyclic, alkyl groups; a hydroxyl group protected as a sulfate mono- or diester bearing a $C_1$–$C_4$ saturated or unsaturated alkyl group; a hydroxyl group protected as a sulfonate ester derived from a sulfonic acid bearing a $C_1$–$C_8$ saturated or unsaturated, cyclic or acyclic, alkyl group; an amino group; a primary or secondary amine bearing 1 to 2 $C_1$–$C_4$ saturated or unsaturated alkyl group(s), respectively; a carboxamide-protected, unsubstituted or primary amino group bearing a $C_1$–$C_4$ saturated or unsaturated alkyl group and derived from a $C_1$–$C_8$ saturated or unsaturated, cyclic or acyclic, carboxylic acid; a carboxylic acid; a carboxylate ester bearing a $C_1$–$C_4$ saturated or unsaturated alkyl group; a phosphonic acid; a phosphonate mono- or diester bearing 1 to 2 $C_1$–$C_4$ saturated or unsaturated alkyl group(s), respectively; a phosphinic acid having a $C_1$–$C_8$ saturated or unsaturated, cyclic or acyclic, alkyl group or ester bearing a $C_1$–$C_4$ saturated or unsaturated alkyl group; a formyl group; an acetyl group; a benzoyl group; a carboxamide group derived from ammonia, or a primary or secondary amine bearing 1 to 2 $C_1$–$C_4$ saturated or unsaturated alkyl group(s), respectively; a sulfhydryl group; a thioether bearing a $C_1$–$C_8$ saturated or unsaturated, cyclic or acyclic, alkyl group; a sulfonic acid, a sulfonate ester bearing a $C_1$–$C_4$ saturated or unsaturated alkyl group; an alkylsulfonyl group bearing a $C_1$–$C_8$ saturated or unsaturated, cyclic or acyclic, alkyl group; a phenylsulfonyl group; a sulfoxide bearing a $C_1$–$C_8$ saturated or unsaturated, cyclic or acyclic, alkyl group; a phenylsulfoxide; a phenylseleno group; a phenylselenoxide; an azide; a halogen; a cyano group; a nitro group; a nitroso group; a diazonium group; or a trifluoromethyl group; $R^9$ is a silyl protecting group; and $R^{10}$ is a $C_4$ protecting group.

9. The process according to claim 1 wherein $R^{10}$ is SEM and $R^9$ is TIPS.

10. An enantiomerically enriched compound corresponding to the formula (I) or (II):

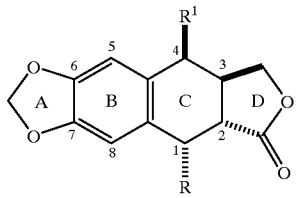

(I)

or

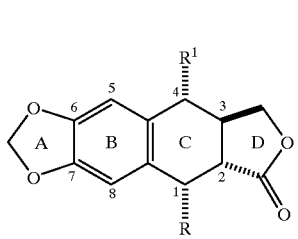

(II)

wherein R is:

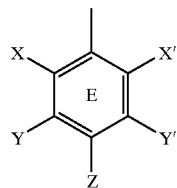

and X X', Y, Y' and Z may each be hydrogen; deuterium; tritium; a $C_1$–$C_8$ saturated or unsaturated, alkyl or cycloalkyl group; a hydroxyl group; an ether-protected hydroxyl group bearing a $C_1$–$C_8$ saturated or unsaturated alkyl or cyclic alkyl group; a carboxylate ester-protected hydroxyl group derived from a $C_1$–$C_8$ saturated or unsaturated, cyclic or acyclic, carboxylic acid; a hydroxyl group protected as a phosphate mono-, di- or triester, the di-, or triester having $C_1$–$C_4$ saturated or unsaturated alkyl group(s); a phosphonate mono- or diester-protected hydroxyl group derived from a $C_1$–$C_8$ saturated or unsaturated, cyclic or acyclic, phosphonic acid wherein the diester also contains a $C_1$–$C_4$ saturated or unsaturated alkyl group; a phosphinate ester-protected hydroxyl group derived from a phosphinic acid bearing two $C_1$–$C_8$ saturated or unsaturated, cyclic or acyclic, alkyl groups; a hydroxyl group protected as a sulfate mono- or diester bearing a $C_1$–$C_4$ saturated or unsaturated alkyl group; a hydroxyl group protected as a sulfonate ester derived from a sulfonic acid bearing a $C_1$–$C_8$ saturated or unsaturated, cyclic or acyclic, alkyl group; an amino group; a primary or secondary amine bearing 1 to 2 $C_1$–$C_4$ saturated or unsaturated alkyl group(s), respectively; a carboxamide-protected, unsubstituted or primary amino group bearing a $C_1$–$C_4$ saturated or unsaturated alkyl group and derived from a $C_1$–$C_8$ saturated or unsaturated, cyclic or acyclic, carboxylic acid; a carboxylic acid; a carboxylate ester bearing a $C_1$–$C_4$ saturated or unsaturated alkyl group; a phosphonic acid; a phosphonate mono- or diester bearing 1 to 2 $C_1$–$C_4$ saturated or unsaturated alkyl group(s), respectively; a phosphinic acid having a $C_1$–$C_8$ saturated or unsaturated, cyclic or acyclic, alkyl group or ester bearing a $C_1$–$C_4$ saturated or unsaturated alkyl group; a formyl group; an acetyl group; a benzoyl group; a carboxamide group derived from ammonia, or a primary or secondary amine bearing 1 to 2 $C_1$–$C_4$ saturated or unsaturated alkyl group(s), respectively; a sulfhydryl group; a thioether bearing a $C_1$–$C_8$ saturated or unsaturated, cyclic or acyclic, alkyl group; a sulfonic acid, a sulfonate ester bearing a $C_1$–$C_4$ saturated or unsaturated alkyl group; an alkylsulfonyl group bearing a $C_1$–$C_8$ saturated or unsaturated, cyclic or acyclic, alkyl group; a phenylsulfonyl group; a sulfoxide bearing a $C_1$–$C_8$ saturated or unsaturated, cyclic or acyclic, alkyl group; a phenylsulfoxide; a phenylseleno group; a phenylselenoxide; an azide; a halogen; a cyano group; a nitro group; a nitroso group; a diazonium group; or a trifluoromethyl group; and with the proviso that only two of Y, Y', and Z can be a hydroxyl or an ether- or ester-protected hydroxyl group; with the further proviso that when X, X', Y, Y' are H, Z cannot be hydrogen, hydroxyl, an alkoxy, or a protected hydroxyl group and when X, X' are H, and Z is hydroxyl, an alkoxy or a protected hydroxyl group, neither Y or Y' can be an alkoxy;

$R^1$ is one of
a) —OH;
b) an ether or a glycoside;
c) a substituted or unsubstituted amine or aniline;
d) a $C_2$ to $C_8$ alkenyl group;
e) a $C_1$ to $C_8$ alcohol;
except the following compounds:
X and X'=H, Y=—OCH$_3$, Y'=H, —NH$_2$, —N$^+$≡N, Cl, Br, I, Z=—OH;
X and X'=H, Y=OCH$_3$, Y'=OCH$_3$, Z=H, Cl or Br;
X and X'=H, Y=OH, Y'=H, Z=OCH$_3$
prepared by
subjecting a compound of formula (a);

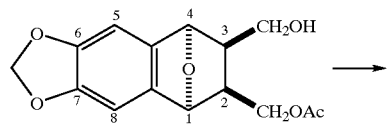
(a)

to silylation, deacetylation, and oxidation to produce a compound of formula (b)

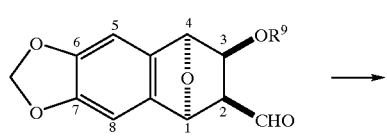
(b)

wherein $R^9$ is a silyl protecting group;
converting the compound of formula (b) to a compound of formula (c) by retro-Michael ring opening and protection of the $C_4$—OH followed by aldehyde oxidation

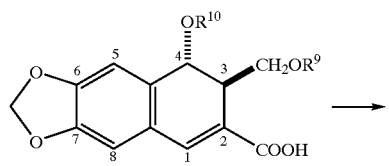
(c)

wherein $R^{10}$ is a $C_4$ protecting group;
converting the compound of formula (c) to a compound of formula (d) by transformation of the carboxylic acid into an acyl oxazolidinone functionality;

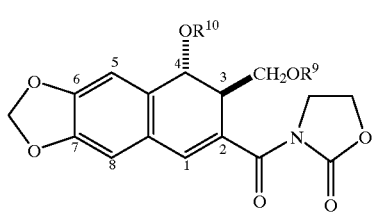
(d)

converting the compound of formula (d) to a compound of formula (e) by Cu$^I$-mediated conjugate addition of RMgBr at a temperature of –10 to 0° C.;

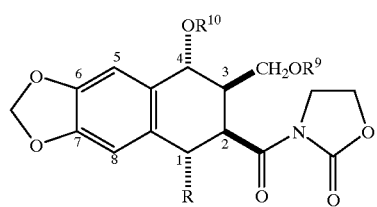
(e)

converting the compound of formula (e) to a compound of formula (f) by chemoselective silyl ether deprotection by heating with a fluoride source and cyclization to produce the corresponding lactone;

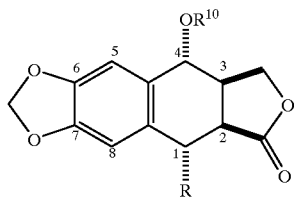
(f)

converting the compound of formula (f) to a compound of formula (I) by generation and kinetic quenching of a $C_2$ enolate and deprotection of the $C_4$OH.

11. The process according to claim 10 wherein $R^1$ is

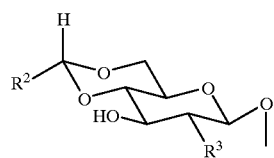

wherein $R^2$ is methyl or thienyl, and $R^3$ is —OH or $N(CH_3)_2$.

12. The process according to claim 10 wherein $R^1$ is

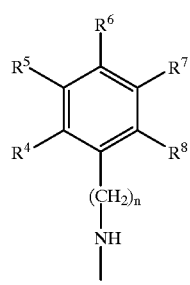

wherein n=0–4 and $R^4$, $R^5$, $R^6$, $R^7$, and $R^8$ are each independently selected from the group consisting of hydrogen; a saturated or unsaturated $C_1$–$C_8$ alkyl or cycloalkyl, optionally substituted with a halogen or hydroxy; a halogen, or a hydroxy; a $C_1$–$C_8$ alkoxy; a $C_1$–$C_8$ alcohol; an ether having $C_1$–$C_8$ alkyl groups; a carboxylate ester having $C_1$–$C_8$ alkyl groups; an amide; a carboxylic acid; an amine, optionally substituted with one or more $C_1$–$C_4$ alkyl group(s); $NH_2.HCl$, $NH_2.HAc$, $NH_2.½H_2SO_4$, $NH_2.⅓H_3PO_4$, $SO_2H$, $SO_2 NH_2$; a cyano group; a phosphate acid or ester having $C_1$–$C_8$ alkyl groups; a phosphonic acid or ester having $C_1$–$C_8$ alkyl groups; a nitro group; a nitroso group; an azide; a sulfone; a sulfoxide; a diazonium salt, phenyl, a substituted phenyl, phenoxy, substituted phenoxy, anilinyl, substituted anilinyl, cyclohexyl, piperidine, or a heterocyclic ring; or any two of $R^4$–$R^8$ may together form a heterocyclic ring.

13. The process according to claim 10 wherein the silylating agent is TIPSCl.

14. The process according to claim 10 wherein the oxidation is Swern oxidation.

15. The process according to claim 10 wherein $R^{10}$ is SEM.

16. The process according to claim 15 wherein the compound of formula (f) is converted to the compound of formula (I) under modified Kim conditions.

17. An enantiomerically enriched compound corresponding to the formula (I) or (II):

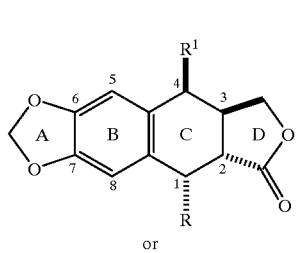

(I)

-continued

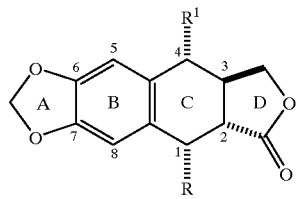

(II)

wherein R is:

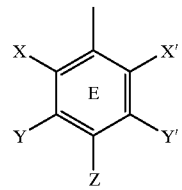

and X, X', Y, Y' and Z may each be hydrogen; deuterium; tritium; a $C_1$–$C_8$ saturated or unsaturated, alkyl or cycloalkyl group; a hydroxyl group; an ether-protected hydroxyl group bearing a $C_1$–$C_8$ saturated or unsaturated alkyl or cyclic alkyl group; a carboxylate ester-protected hydroxyl group derived from a $C_1$–$C_8$ saturated or unsaturated, cyclic or acyclic, carboxylic acid; a hydroxyl group protected as a phosphate mono-, di- or triester, the di-, or triester having $C_1$–$C_4$ saturated or unsaturated alkyl group(s); a phosphonate mono- or diester-protected hydroxyl group derived from a $C_1$–$C_8$ saturated or unsaturated, cyclic or acyclic, phosphonic acid wherein the diester also contains a $C_1$–$C_4$ saturated or unsaturated alkyl group; a phosphinate ester-protected hydroxyl group derived from a phosphinic acid bearing two $C_1$–$C_8$ saturated or unsaturated, cyclic or acyclic, alkyl groups; a hydroxyl group protected as a sulfate mono- or diester bearing a $C_1$–$C_4$ saturated or unsaturated alkyl group; a hydroxyl group protected as a sulfonate ester derived from a sulfonic acid bearing a $C_1$–$C_8$ saturated or unsaturated, cyclic or acyclic, alkyl group; an amino group; a primary or secondary amine bearing 1 to 2 $C_1$–$C_4$ saturated or unsaturated alkyl group(s), respectively; a carboxamide-protected, unsubstituted or primary bearing a $C_1$–$C_4$ saturated or unsaturated alkyl group; amino group derived from a $C_1$–$C_8$ saturated or unsaturated, cyclic or acyclic, carboxylic acid; a carboxylic acid; a carboxylate ester bearing a $C_1$–$C_4$ saturated or unsaturated alkyl group; a phosphonic acid; a phosphonate mono- or diester bearing 1 to 2 $C_1$–$C_4$ saturated or unsaturated alkyl group(s), respectively; a phosphinic acid having a $C_1$–$C_8$ saturated or unsaturated, cyclic or acyclic, alkyl group or ester bearing a $C_1$–$C_4$ saturated or unsaturated alkyl group; a formyl group; an acetyl group; a benzoyl group; a carboxamide group derived from ammonia, or a primary or secondary amine bearing 1 to 2 $C_1$–$C_4$ saturated or unsaturated alkyl group(s), respectively; a sulfhydryl group; a thioether bearing a $C_1$–$C_8$ saturated or unsaturated, cyclic or acyclic, alkyl group; a sulfonic acid, a sulfonate ester bearing a $C_1$–$C_4$ saturated or unsaturated alkyl group; an alkylsulfonyl group bearing a $C_1$–$C_8$ saturated or unsaturated, cyclic or acyclic, alkyl group; a phenylsulfonyl group; a sulfoxide bearing a $C_1$–$C_8$ saturated or unsaturated, cyclic or acyclic, alkyl group; a phenylsulfoxide; a phenylseleno group; a phenylselenoxide; an azide; a halogen; a cyano group; a nitro group; a nitroso group; a diazonium group; or a trifluoromethyl group;

with the proviso that only one of Y, Y', and Z can be a hydroxyl or an ether- or ester-protected hydroxyl group; with the further proviso that when X, X', Y, Y' are H, Z cannot be hydrogen, hydroxyl, an alkoxy, or a protected hydroxyl group; and R is one of
a) —OH;
b) an ether or a glycoside;
c) a substituted amine or aniline;
d) a $C_2$ to $C_8$ alkenyl;
e) a $C_1$ to $C_8$ alcohol.

18. The compound of claim 17 wherein $R^1$ is

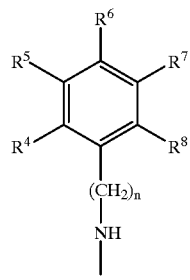

wherein $R^2$ is methyl or thienyl, and $R^3$ is —OH or $N(CH_3)_2$.

19. The compound of claim 17 wherein $R^1$ is

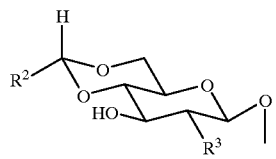

wherein n=0–4 and $R^4$, $R^5$, $R^6$, $R^7$, and $R^8$ are each independently selected from the group consisting of hydrogen; a saturated or unsaturated $C_1$–$C_8$ alkyl or cycloalkyl, optionally substituted with a halogen or hydroxy; a halogen, or a hydroxy; a $C_1$–$C_8$ alkoxy; a $C_1$–$C_8$ alcohol; an ether having $C_1$–$C_8$ alkyl groups; a carboxylate ester having $C_1$–$C_8$ alkyl groups; an amide; a carboxylic acid; an amine, optionally substituted with one or more $C_1$–$C_4$ alkyl group(s); $NH_2 \cdot HCl$, $NH_2 \cdot HAc$, $NH_2 \cdot \frac{1}{2}H_2SO_4$, $NH_2 \cdot \frac{1}{3}H_3PO_4$, $SO_2H$, $SO_2NH_2$; a cyano group; a phosphate acid or ester having $C_1$–$C_8$ alkyl groups; a phosphonic acid or ester having $C_1$–$C_8$ alkyl groups; a nitro group; a nitroso group; an azide; a sulfone; a sulfoxide; a diazonium salt, phenyl, a substituted phenyl, phenoxy, substituted phenoxy, anilinyl, substituted anilinyl, cyclohexyl, piperidine, or a heterocyclic ring; or any two of $R^4$–$R^8$ may together form a heterocyclic ring.

20. An enantiomerically enriched compound corresponding to the formula (I) or (II):

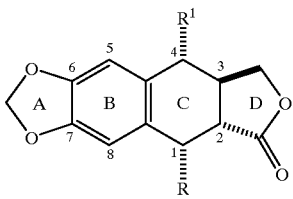

(I)

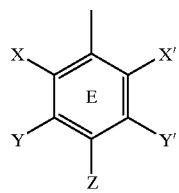

(II)

wherein R is:

and X, X', Y, Y' and Z may each be hydrogen; deuterium; tritium; a $C_1$–$C_8$ saturated or unsaturated, alkyl or cycloalkyl group; a hydroxyl group; an ether-protected hydroxyl group bearing a $C_1$–$C_8$ saturated or unsaturated alkyl or cyclic alkyl group; a carboxylate ester-protected hydroxyl group derived from a $C_1$–$C_8$ saturated or unsaturated, cyclic or acyclic, carboxylic acid; a hydroxyl group protected as a phosphate mono-, di- or triester, the di-, or triester having $C_1$–$C_4$ saturated or unsaturated alkyl group(s); a phosphonate mono- or diester-protected hydroxyl group derived from a $C_1$–$C_8$ saturated or unsaturated, cyclic or acyclic, phosphonic acid wherein the diester also contains a $C_1$–$C_4$ saturated or unsaturated alkyl group; a phosphinate ester-protected hydroxyl group derived from a phosphinic acid bearing two $C_1$–$C_8$ saturated or unsaturated, cyclic or acyclic, alkyl groups; a hydroxyl group protected as a sulfate mono- or diester bearing a $C_1$–$C_4$ saturated or unsaturated alkyl group; a hydroxyl group protected as a sulfonate ester derived from a sulfonic acid bearing a $C_1$–$C_8$ saturated or unsaturated, cyclic or acyclic, alkyl group; an amino group; a primary or secondary amine bearing 1 to 2 $C_1$–$C_4$ saturated or unsaturated alkyl group(s), respectively; a carboxamide-protected, unsubstituted or primary bearing a $C_1$–$C_4$ saturated or unsaturated alkyl group; amino group derived from a $C_1$–$C_8$ saturated or unsaturated, cyclic or acyclic, carboxylic acid; a carboxylic acid; a carboxylate ester bearing a $C_1$–$C_4$ saturated or unsaturated alkyl group; a phosphonic acid; a phosphonate mono- or diester bearing 1 to 2 $C_1$–$C_4$ saturated or unsaturated alkyl group(s), respectively; a phosphinic acid having a $C_1$–$C_8$ saturated or unsaturated, cyclic or acyclic, alkyl group or ester bearing a $C_1$–$C_4$ saturated or unsaturated alkyl group; a formyl group; an acetyl group; a benzoyl group; a carboxamide group derived from ammonia, or a primary or secondary amine bearing 1 to 2 $C_1$–$C_4$ saturated or unsaturated alkyl group(s), respectively; a sulfhydryl group; a thioether bearing a $C_1$–$C_8$ saturated or unsaturated, cyclic or acyclic, alkyl group; a sulfonic acid, a sulfonate ester bearing a $C_1$–$C_4$ saturated or unsaturated alkyl group; an alkylsulfonyl group bearing a $C_1$–$C_8$ saturated or unsaturated, cyclic or acyclic, alkyl group; a phenylsulfonyl group; a sulfoxide bearing a $C_1$–$C_8$ saturated or unsaturated, cyclic or acyclic, alkyl group; a phenylsulfoxide; a phenylseleno group; a phenylselenoxide; an azide; a halogen; a cyano group; a nitro group; a nitroso group; a diazonium group; or a trifluoromethyl group;

with the proviso that only two of Y, Y', and Z can be a hydroxyl or an ether- or ester-protected hydroxyl group; with the further proviso that when X, X', Y, Y' are H, Z cannot be hydrogen, hydroxyl, an alkoxy, or a protected hydroxyl group and when X, X' are H, and Z is hydroxyl, an alkoxy or a protected hydroxyl group, neither Y or Y' can be an alkoxy; and R is one of a) —OH;

b) an ether or a glycoside;

c) A substituted or unsubstituted amine or aniline;

d) a $C_2$ to $C_8$ alkenyl;

e) a $C_1$ to $C_8$ alcohol;

except the following compounds:

X and X'=H, Y=—$OCH_3$, Y'=H, —$NH_2$, —$N^+$≡N, Cl, Br, I, Z=—OH;

X and X'=H, Y=$OCH_3$, Y'=$OCH_3$, Z=H, Cl or Br;

X and X'=H, Y=OH, Y'=H, Z=$OCH_3$.

21. The compound of claim 20 wherein $R^1$ is

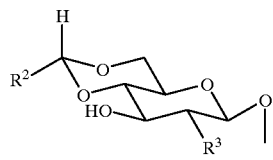

wherein $R^2$ is methyl or thienyl, and $R^3$ is —OH or $N(CH_3)_2$.

22. The compound of claim 20 wherein $R^1$ is

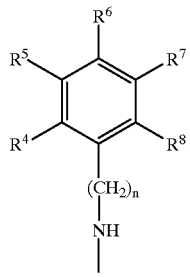

wherein n=0–4 and $R^4$, $R^5$, $R^6$, $R^7$, and $R^8$ are each independently selected from the group consisting of hydrogen; a saturated or unsaturated $C_1$–$C$alkyl or cycloalkyl, optionally substituted with a halogen or hydroxy; a halogen, or a hydroxy; a $C_1$–$C_8$ alkoxy; a $C_1$–$C_8$ alcohol; an ether having $C_1$–$C_8$ alkyl groups; a carboxylate ester having $C_1$–$C_8$ alkyl groups; an amide; a carboxylic acid; an amine, optionally substituted with one or more $C_1$–$C_4$ alkyl group(s); $NH_2.HCl$, $NH_2.HAc$, $NH_2.½H_2SO_4$, $NH_2.⅓H_3PO_4$, $SO_2H$, $SO_2NH_2$; a cyano group; a phosphate acid or ester having $C_1$–$C_8$ alkyl groups; a phosphonic acid or ester having $C_1$–$C_8$ alkyl groups; a nitro group; a nitroso group; an azide; a sulfone; a sulfoxide; a diazonium salt, phenyl, a substituted phenyl, phenoxy, substituted phenoxy, anilinyl, substituted anilinyl, cyclohexyl, piperidine, or a heterocyclic ring; or any two of $R^4$–$R^8$ may together form a heterocyclic ring.

23. The process according to claim 1 wherein $R^1$ is —$CH_2CH=CH_2$ or —$CH_2CH_2CH_2OH$.

24. The compound according to claim 10 wherein $R^1$ is —$CH_2CH=CH_2$ or —$CH_2CH_2CH_2OH$.

25. The compound according to claim 17 wherein $R^1$ is —$CH_2CH=CH_2$ or —$CH_2CH_2CH_2OH$.

26. The compound according to claim 20 wherein $R^1$ is —$CH_2CH=CH_2$ or —$CH_2CH_2CH_2OH$.

27. A pharmaceutical composition comprising the compound of claims 10, 17, or 20 and a pharmaceutically acceptable carrier.

* * * * *

UNITED STATES PATENT AND TRADEMARK OFFICE
CERTIFICATE OF CORRECTION

PATENT NO.    : 6,051,721
DATED         : April 28, 2000
INVENTOR(S)   : David Berkowitz It is certified that error appears in the above-identified patent and that said Letters Patent is hereby corrected as shown below:

Claim 3, column 22,
Line 25: "allyl" has been replaced by -- alkyl --;
Line 26: "SO$_2$K," has been replaced by -- SO$_2$H, --;

Claim 8, column 23,
Line 28: "C" has been replaced by -- C$_8$ --;
Line 32: "C" has been replaced by -- C$_8$ --.

Signed and Sealed this

Eleventh Day of September, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,051,721 | Page 1 of 1 |
| APPLICATION NO. | : 08/942640 | |
| DATED | : April 18, 2000 | |
| INVENTOR(S) | : David Berkowitz | |

It is certified that error appears in the above-identified patent and that said Letters Patent is hereby corrected as shown below:

In the Claims; Claim 11; Column 27; Line 1:
    Please delete "process" and insert --compound--

Claim 12; Column 27; Line 13:
    Please delete "process" and insert --compound--

Claim 13; Column 27; Line 44:
    Please delete "process" and insert --compound--

Claim 14; Column 27; Line 46:
    Please delete "process" and insert --compound--

Claim 16; Column 27; Line 51:
    Please delete "process" and insert --compound--

Claim 17; Column 29; Line 6:
    Please delete "R" and insert -- $R^1$ --

Signed and Sealed this

First Day of May, 2007

JON W. DUDAS
*Director of the United States Patent and Trademark Office*